US00PP36321P2

(12) United States Plant Patent
Smutzer

(10) Patent No.: US PP36,321 P2
(45) Date of Patent: Dec. 17, 2024

(54) ***CUPRESSUS* PLANT NAMED 'GRECQF'**

(50) Latin Name: *Cupressus arizonica*
Varietal Denomination: GRECQF

(71) Applicant: Greenleaf Nursery Company, Park Hill, OK (US)

(72) Inventor: Harry J Smutzer, El Campo, TX (US)

(73) Assignee: GREENLEAF NURSERY COMPANY, Park Hill, OK (US)

( * ) Notice: Subject to any disclaimer, the term of this patent is extended or adjusted under 35 U.S.C. 154(b) by 0 days.

(21) Appl. No.: 18/586,469

(22) Filed: Feb. 24, 2024

(51) Int. Cl.
*A01H 5/12* (2018.01)
*A01H 7/00* (2006.01)

(52) U.S. Cl.
USPC ..... Plt./213

(58) Field of Classification Search
USPC ..... Plt./213
See application file for complete search history.

*Primary Examiner* — Karen M Redden
*Assistant Examiner* — Zachariah Allan Kay
(74) *Attorney, Agent, or Firm* — Penny J. Aguirre

(57) ABSTRACT

A new cultivar of *Cupressus* plant named 'GRECQF' that is characterized by its foliage that is blue-silver in color, its highly vigorous growth rate, its fullness in its natural form with minimal shearing, its very high propagation success rate, and its good resistance to fungal blight.

2 Drawing Sheets

Botanical classification: *Cupressus arizonica.*
Varietal denomination: 'GRECQF'.

BACKGROUND OF THE INVENTION

The present invention relates to a new and distinct cultivar of *Cupressus arizonica* and will be referred to hereafter by its cultivar name, 'GRECQF'. 'GRECQF' is a new cultivar of Arizona cypress tree grown for landscape use.

The Inventor discovered the new cultivar in March of 2019 as a naturally occurring branch mutation of *Cupressus* 'Blue Steel' (not patented) in a container block at his nursery in El Campo, Texas.

Asexual propagation of the new cultivar was first accomplished by semi-hardwood stem cuttings by the Inventor in El Campo, Texas in January of 2020. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRECQF', as a unique cultivar of *Cupressus.*

1. 'GRECQF' exhibits foliage that is blue-silver in color.
2. 'GRECQF' exhibits a highly vigorous growth rate.
3. 'GRECQF' exhibits fullness in its natural form with minimal shearing.
4. 'GRECQF' exhibits a very high propagation success rate.
5. 'GRECQF' exhibits good resistance to fungal blights.

The female parent plant of 'GRECQF' differs from 'GRECQF' in having foliage that is less blue in color, a much lower propagation success rate, a greater need for shearing to obtain dense foliage, a slower growth rate, and lower disease resistance. 'GRECQF' can be most closely compared to *Cupressus arizonica* cultivars 'Blue Ice' (not patented) and 'Carolina Sapphire' (not patented). 'Blue Ice' is similar to 'GRECQF' in plant size and in being a low maintenance cultivar. 'Blue Ice' differs from 'GRECQF' in having deeper blue and less silvery colored foliage, a more open and leggier appearance, a slower growth rate, and a lower rooting percentage rate. 'Carolina Sapphire' is similar to 'GRECQF' in having a vigorous growth rate and in being a low maintenance cultivar. 'Carolina Sapphire' differs from 'GRECQF' in having turquoise-gray colored foliage, more susceptibility to fungal blight, a smaller plant size, and a lower rooting percentage rate.

BRIEF DESCRIPTION OF THE DRAWINGS

The accompanying color photographs illustrates the overall appearance and distinct characteristics of the new *Cupressus.*

The photograph in FIG. 1 was taken of a 3.5-year-old plant of 'GRECQF' as grown outdoors in a 15-gallon container in El Campo, Texas and provides a view of the foliage coloration and plant habit of 'GRECQF'.

Figure 1:
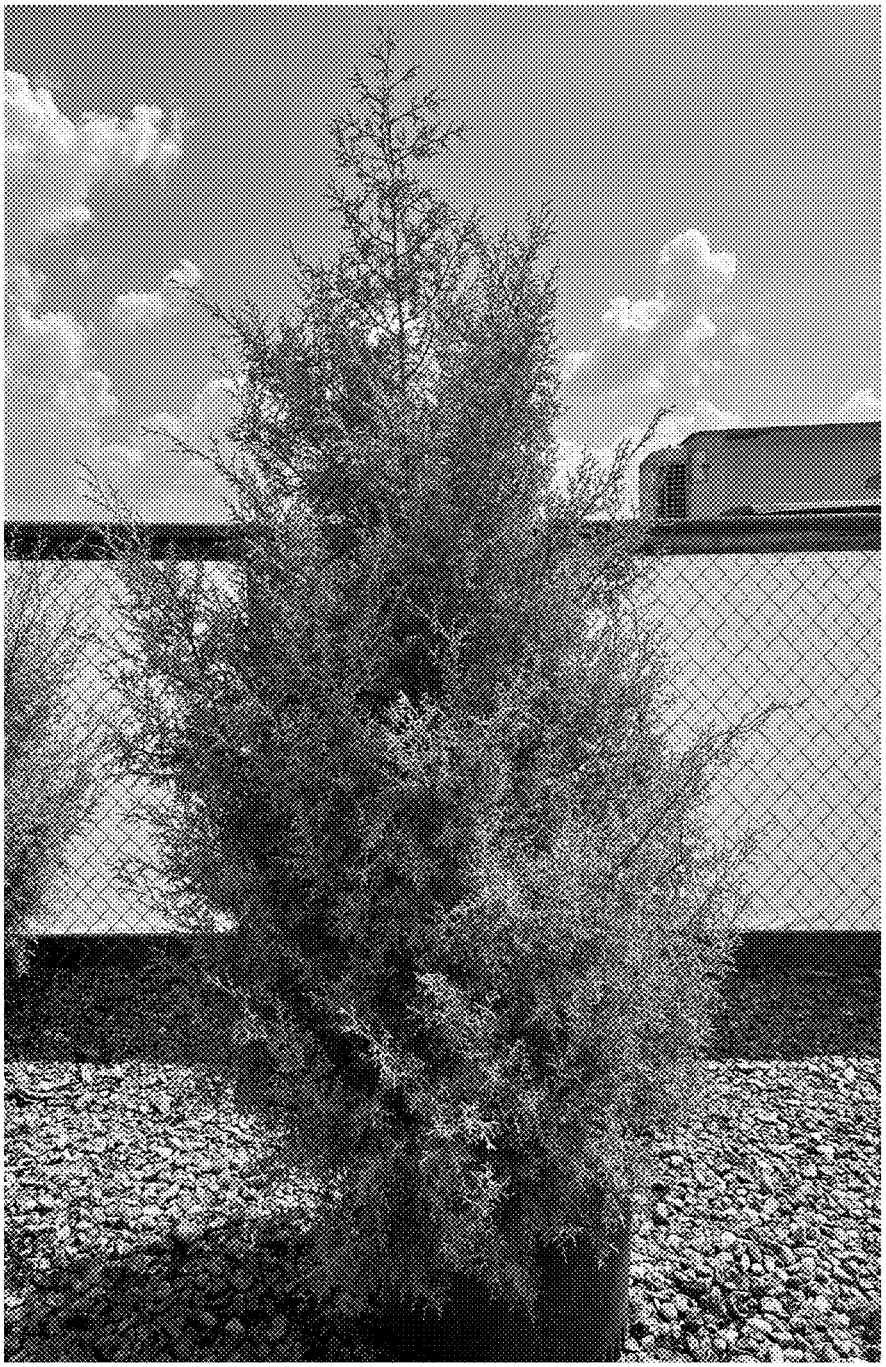
Figure 2:
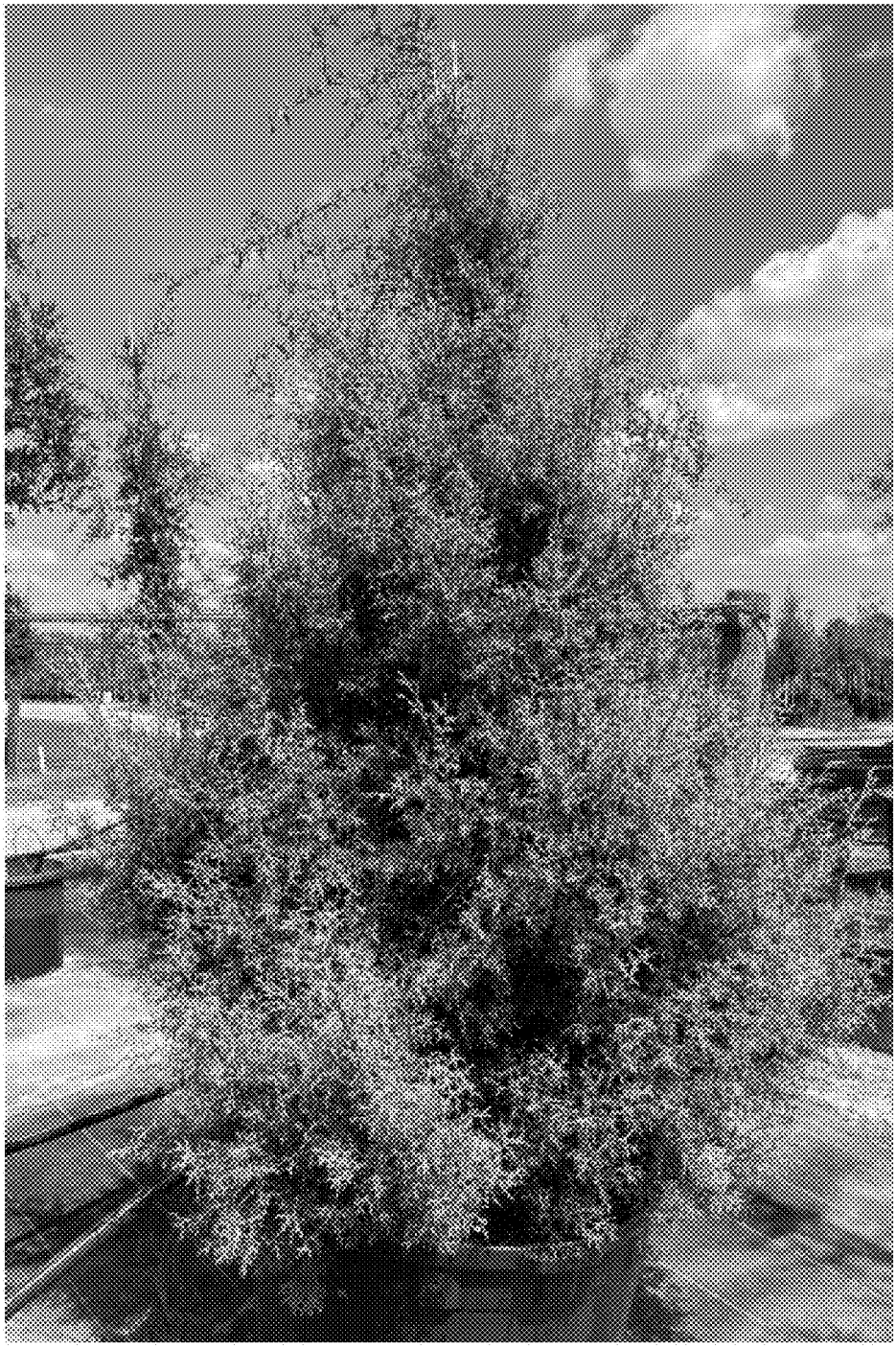

The photograph in FIG. 2 was taken of a 4.5-year-old plant of 'GRECQF' as grown outdoors in a 45-gallon container in El Campo, Texas and provides a view of the foliage coloration and plant habit of 'GRECQF'.

The colors in the photographs are as close as possible with the photographic and printing technology utilized and the values cited in the detailed botanical description accurately describe the colors of the new cultivar.

DETAILED BOTANICAL DESCRIPTION

The following is a detailed description of 18-month-old plants of the new cultivar as grown outdoors in 15-gallon containers in El Campo, Texas. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Coniferous evergreen tree.

*Growth habit*.—Upright, full appearance with minimal shearing, ovate shape when mature.

*Height and spread*.—An average of 1.55 m in height and 72 cm in width as an 18-month-old plant as grown in a container, reaches 9 m in height and 4.6 m in width when grown in the landscape.

*Hardiness*.—At least in U.S.D.A. Zones 6 to 10.

*Diseases and pests*.—Good resistance has been observed to *Phomopsis* blight (caused by *Phomopsis juniperovora*) and to Pestalotia blight (caused by *Pestalotiopsis palmarum*), a fungal disease that is typically observed secondary to crop environmental stresses.

*Root description*.—Fibrous, fine and well-branched, N167C in color.

*Propagation*.—Semi-hardwood stem cuttings.

*Root development*.—Roots initiate in 4 to 5 months and will fully develop in a 2 gallon container in about 12 months.

*Growth rate*.—Highly vigorous.

Branch description:

*Branching*.—Very freely branching, main branch; 1, vertical, lateral branches; 30, angles ranging between 45° and 55°, slightly curved and drooping, tertiary branches; 24 per lateral branch, held in a 45° angle to lateral branch.

*Branching arrangement*.—Alternate, whorled.

*Branch surface* (*texture*).—Young and mature branches covered with scale-like leaves, young branches are slightly glossy, older branches are matte, trunk is matte, glabrous.

*Branch shape*.—Rounded.

*Branch size*.—Main branch; 1.2 m in length, 1.5 cm in diameter, trunk diameter; 3 cm, lateral branches; average of 73 cm in length, 7 mm in diameter, tertiary branches; 5 cm in length, 2 mm in diameter.

*Internode length*.—Average of 3 cm.

*Branch color*.—Young; a blend of 151A, 150A, and 145A, aging and turning to N170A, mature; N199A, flushed with N200A, old wood and trunk; N200B.

*Branch strength*.—Main branch; very strong, lateral branches; strong, bendable.

Foliage description:

*Leaf arrangement*.—Alternate.

*Leaf shape*.—Lanceolate, flattened and slightly rounded.

*Leaf aspect*.—Held in a 45° angle to tertiary branch.

*Leaf division*.—Simple.

*Leaf base*.—Decurrent.

*Leaf apex*.—Bluntly acute to rounded.

*Leaf venation*.—Not visible.

*Leaf margins*.—Entire.

*Leaf surface*.—Both surfaces are glossy, covered in scale-like adpressed leaves.

*Leaf color*.—Young both surfaces; 144A to 144B, mature both surfaces; 122C and 122A.

*Leaf fragrance*.—Strong fragrance, typical for *Cupressus macrocarpa*.

*Leaf size*.—An average of 1 cm in length and 2 mm in width.

*Leaf quantity*.—10 per tertiary branch, over 80 scale-like leaves per leaf.

*Durability to stresses*.—High.

Cone description: No cones have been produced to date.

It is claimed:

1. A new and distinct cultivar of *Cupressus* plant named 'GRECQF' as herein illustrated and described.

* * * * *